United States Patent
MacDonald et al.

(10) Patent No.: US 9,757,523 B2
(45) Date of Patent: Sep. 12, 2017

(54) SELECTABLE DOSE INJECTION DEVICE

(71) Applicant: OWEN MUMFORD LIMITED, Oxfordshire (GB)

(72) Inventors: Elizabeth MacDonald, Chichester (GB); Lee Thomas Smith, Stafford (GB); Joe David Cowan, Staffordshire (GB); Matthew Farmer, Oxfordshire (GB)

(73) Assignee: OWEN MUMFORD LIMITED, Oxfordshire (GB)

( * ) Notice: Subject to any disclaimer, the term of this patent is extended or adjusted under 35 U.S.C. 154(b) by 0 days.

(21) Appl. No.: 15/178,695

(22) Filed: Jun. 10, 2016

(65) Prior Publication Data

US 2016/0279343 A1 Sep. 29, 2016

Related U.S. Application Data

(63) Continuation of application No. PCT/GB2014/053696, filed on Dec. 12, 2014.

(30) Foreign Application Priority Data

Dec. 13, 2013 (GB) .................................. 1322110.6

(51) Int. Cl.
*A61M 5/315* (2006.01)
*A61M 5/20* (2006.01)
(Continued)

(52) U.S. Cl.
CPC ...... *A61M 5/31501* (2013.01); *A61M 5/2033* (2013.01); *A61M 5/24* (2013.01);
(Continued)

(58) Field of Classification Search
CPC ........ A61M 5/2033; A61M 2005/3247; A61M 2005/2013; A61M 2005/2073;
(Continued)

(56) References Cited

U.S. PATENT DOCUMENTS 4,865,591 A * 9/1989 Sams ................ A61M 5/31553
222/287
5,084,017 A 1/1992 Maffetone
(Continued)

FOREIGN PATENT DOCUMENTS

EP 1 968 670 B1 9/2008
EP 2 399 631 A1 12/2011
(Continued)

OTHER PUBLICATIONS

International Search Report, dated Jul. 14, 2015, from corresponding PCT application.
(Continued)

*Primary Examiner* — Gerald Landry, II
(74) *Attorney, Agent, or Firm* — Young & Thompson

(57) ABSTRACT

A substance delivery device for delivering a substance from a container includes a body, and a plunger movable with respect to the body so as to expel at least a portion of a substance from the container, a trigger mechanism, a latch member latched in a stationary position at least along the longitudinal axis of the device before use, and a lockout shroud movable along the longitudinal axis relative to the latch mechanism. User manipulation of the trigger mechanism causes the latch mechanism to become unlatched and move along the longitudinal axis and to cause movement of a plunger relative to the body, and in a first position of the lockout shroud along the longitudinal axis relative to the latch member, the lockout shroud prevents the trigger mechanism from unlatching the latch member, whereas in a second position the lockout shroud allows the trigger mechanism to unlatch the latch member.

15 Claims, 7 Drawing Sheets

(51) Int. Cl.
*A61M 5/50* (2006.01)
*A61M 5/24* (2006.01)
*A61M 5/32* (2006.01)
*A61M 5/31* (2006.01)

(52) U.S. Cl.
CPC ........ *A61M 5/3153* (2013.01); *A61M 5/3155* (2013.01); *A61M 5/3156* (2013.01); *A61M 5/3158* (2013.01); *A61M 5/31525* (2013.01); *A61M 5/31553* (2013.01); *A61M 5/31591* (2013.01); *A61M 5/3204* (2013.01); *A61M 5/3213* (2013.01); *A61M 5/5086* (2013.01); *A61M 5/31578* (2013.01); *A61M 2005/206* (2013.01); *A61M 2005/208* (2013.01); *A61M 2005/2013* (2013.01); *A61M 2005/2073* (2013.01); *A61M 2005/2403* (2013.01); *A61M 2005/3125* (2013.01); *A61M 2005/3247* (2013.01)

(58) Field of Classification Search
CPC .............. A61M 5/3257; A61M 5/3202; A61M 5/3243; A61M 5/3271; A61M 5/3158
USPC ................ 604/110, 131, 135, 192, 198, 208
See application file for complete search history.

(56) References Cited

U.S. PATENT DOCUMENTS

| | | | |
|---|---|---|---|
| 5,486,164 A * | 1/1996 | Streck | A61M 5/3243 604/198 |
| 5,807,346 A | 9/1998 | Frezza | |
| 6,132,401 A * | 10/2000 | Van Der Meyden | A61M 5/2429 604/110 |
| 6,805,686 B1 * | 10/2004 | Fathallah | A61M 5/2033 604/134 |
| 2002/0045866 A1 * | 4/2002 | Sadowski | A61M 5/2425 604/208 |
| 2004/0215151 A1 * | 10/2004 | Marshall | A61M 5/2033 604/198 |
| 2006/0270985 A1 | 11/2006 | Hommann et al. | |
| 2007/0239117 A1 * | 10/2007 | Chelak | A61M 5/326 604/198 |
| 2008/0103453 A1 * | 5/2008 | Liversidge | A61M 5/326 604/187 |
| 2010/0010454 A1 * | 1/2010 | Marshall | A61M 5/2033 604/208 |
| 2012/0323177 A1 * | 12/2012 | Adams | A61M 5/2033 604/135 |
| 2013/0204195 A1 * | 8/2013 | Ekman | A61M 5/2033 604/197 |
| 2013/0211338 A1 * | 8/2013 | Roberts | A61M 5/326 604/198 |
| 2013/0226085 A1 * | 8/2013 | Roberts | A61M 5/326 604/110 |
| 2014/0039403 A1 * | 2/2014 | Mercer | A61M 5/2448 604/191 |
| 2014/0135705 A1 * | 5/2014 | Hourmand | A61M 5/3257 604/196 |
| 2014/0180216 A1 * | 6/2014 | Lin Lee | A61M 5/315 604/195 |
| 2014/0207073 A1 * | 7/2014 | Shang | A61M 5/2033 604/189 |
| 2014/0221936 A1 * | 8/2014 | Edhouse | A61M 5/31533 604/198 |
| 2014/0257194 A1 * | 9/2014 | Edhouse | A61M 5/20 604/198 |
| 2015/0320640 A1 * | 11/2015 | Christensen | A61M 5/002 29/428 |

FOREIGN PATENT DOCUMENTS

| | | |
|---|---|---|
| EP | 2 633 874 A1 | 9/2013 |
| WO | 00/62839 A2 | 10/2000 |
| WO | 03/011378 A1 | 2/2003 |
| WO | 2005/044346 A2 | 5/2005 |
| WO | 2013/152323 A1 | 10/2013 |

OTHER PUBLICATIONS

GB Search Report, dated Jul. 18, 2014, from corresponding GB application.

* cited by examiner

SELECTABLE DOSE INJECTION DEVICE

FIELD OF THE INVENTION

The present invention relates to injection devices with a mechanical interlock and, in particular, though not necessarily, to such injection devices for delivering a single dose of medicament.

BACKGROUND OF THE INVENTION

WO-A-03/011378 discloses an injection device where a syringe is enclosed in a housing of barrel-like form, the syringe being propelled forward by a drive mechanism to project its needle, followed by continued operation of the drive mechanism to push the plunger of the syringe and eject a dose. This procedure will leave the needle sticking-out, unless certain measures are taken. One answer is to have an arrangement for withdrawing the syringe back into the housing, while another is to have a needle shroud that moves out from the housing to enclose the needle. Of course, this must not interfere with the actual injection operation. It has therefore been proposed that the shroud is normally spring urged forwardly to a needle protecting position, but when the device is pushed against the patient's skin the shroud is forced to retract against its spring. After injection, the spring pushes the shroud forwards again. A mechanism is provided for automatically locking the shroud at its fully projecting position after the injection but not before. The device of WO-A-03/011378 comprises a housing for the syringe, a needle-shroud captive to the leading end of the housing and movable before use between extended and retracted positions, a drive member releasable from a rearward position within the housing to urge the syringe forwards to project its needle beyond the retracted needle shroud and then to express a dose through the needle, and locating members on the housing for capturing the drive member at its forward position attained after expressing the dose, and wherein the captured drive member is arranged to block retraction of the needle shroud from its extended position.

EP-A-1968670 discloses a substance delivery device (auto-injector) for use with a container (such as a syringe) containing the substance, the device comprising a body arranged to house or hold the container; a plunger which is movable with respect to at least a portion of the body, the plunger being arranged to act upon the container so as to move the container with respect to said portion of the body; wherein the plunger is also arranged to expel at least a portion of the substance from the container; and wherein the device comprises means for adjusting the amount of substance to be expelled from the container. The device can also have means for priming the container, and can accommodate containers of different size or shape.

FIG. 6 is a sectional view of an embodiment of the device disclosed in EP-A-1968670. The injection device 1 comprises a body or housing 2, which has three portions. These are (in the order from the proximal end of device 1 to the distal end): a main body 10, a mid-body 13 and a shroud retainer 15, the main body 10 is subdivided into a proximal main body portion 11 and a distal main body portion 12. These portions can be formed as one piece. The housing 2 carries or houses a sleeve-like syringe carrier 82, which is an example of a container carrier. The syringe carrier 82 in turn carries a syringe 20 (or other container for a substance). Syringe 20 comprises a generally cylindrical container portion 24 for accommodating a fluid 22, and a cannula 26. The needle is in communication with the interior of container portion 24 so that the fluid 22 may be expelled through cannula 26. A bung 28 is inserted in the container portion 24 at the proximal end. The bung 28 seals the fluid 22 within the container portion 24. Syringe 20 is biased towards the proximal end by means of spring 23. This spring 23 is however relatively weak. Cannula 26 is initially protected by a needle sheath 29.

A safety cap or needle sheath remover 30 is provided at the distal end of injection device 1. This safety cap 30 is carried by the shroud retainer 15 of housing 2. Towards its proximal end the safety cap 30 is hooked over the proximal end of needle sheath 29 so that, when safety cap 30 is removed, the needle sheath is removed as well.

The distal end of injection device 1 is also provided with a needle guard 32 or "lockout shroud". This needle guard 32 is moveable along the longitudinal axis of the injection device over a limited range. The needle guard 32 is initially covered, and prevented from moving, by safety cap 30. Only once safety cap 30 has been removed (as will be explained below) can needle guard 32 move.

Towards the proximal end of injection device 1 there is provided a plunger 40, which has a distal portion 41 and a proximal portion 42. The plunger is biased by spring 50 towards the distal direction. This bias is relatively strong, and much stronger than the bias provided by spring 23.

At the very proximal end of injection device 1 there is provided a firing button assembly. Its structure and function will be explained below.

The core principle of operation and much of the structure of the injection device 1 is very similar to the technique disclosed in WO 03/011378. Essentially, as in that earlier document, after removal of the safety cap 30 (and needle sheath 29) the needle guard 32 extends in distal direction because of the bias provided by a spring 34. The distal end of the injection device 1 is then pressed against a patient's skin. This pushes needle guard 32 in proximal direction against the bias of spring 34. However, during this action the cannula 26 does not project beyond the distal end of needle guard 32.

As in the earlier-disclosed technique, when the firing button is depressed the plunger 40 is released and can move in distal direction. When the front surface 45 of plunger 40 contacts bung 28, continued movement of the plunger in distal direction initially moves syringe 20 (i.e. not just bung 28) in distal direction. This is so because the force required to move bung 28 in distal direction with respect to container portion 24 is greater than the force required to move the entire syringe 20 in distal direction (to this end the interior surface of the container portion 24 can be provided with circumferential ribs or other friction increasing formations). During this movement of syringe 20 the cannula 26 penetrates the skin of the patient. Eventually the movement in distal direction of syringe 20 comes to a halt, but plunger 40 is still able to move further in distal direction. This leads to bung 28 being moved in distal direction with respect to container portion 24, which means that fluid 22 is expelled from container portion 24 through cannula 26 into the patient. Hence the movement of the syringe 20 (as a whole) and the movement of bung 28 within syringe 20 is brought about by plunger 40 acting on bung 28. It will be appreciated that the portion of plunger 40 (i.e. distal end surface 45) which acts on the syringe 20 to move the syringe is the same as the portion of the plunger which acts on the syringe to move bung 28 so as to expel the fluid. When the plunger 40 has its movement in distal direction stopped the injection operation has been completed. The user can then move the injection device 1 in proximal direction so as to withdraw the needle from the injection site. As the injection device 1 is withdrawn from the skin of the patient the needle guard 32 is moved in distal direction due to the bias provided by spring 34. The guard 32 then locks in the distal position rendering the device safe. The injection device 1 can then be disposed of.

In contrast to the earlier-disclosed injection device, EP-A-1968670 discloses several additional features. Most notably these additional features are an adjustment means for adjusting the dose to be injected, and a priming function.

The adjustment means of EP-A-1968670 primarily comprises a stop member 44 carried by the distal plunger portion 41. Stop member 44 may be provided with an internal thread co-operating with an external thread 43 on the circumferential surface of the distal plunger portion 41. Additionally, stop member 44 is keyed at 46 to the inner surface of distal housing portion 12. With stop member 44 being threadibly engaged with the distal plunger portion 41 and being keyed to distal housing portion 12 (e.g. by means of splines or similar, not shown), the stop member 44 will move in distal or proximal direction when distal plunger portion 41 is rotated about its longitudinal axis.

Distal plunger portion 41 can be rotated by means of adjustment ring 48. Adjustment ring 48 is keyed to a relatively large diameter proximal portion 49 of the plunger 40. This means that, on rotation of adjustment ring 48, the distal plunger portion 41 will carry out the same rotation, but the distal plunger portion 41 is substantially free to move in a direction parallel to the plunger axis, independently from adjustment ring 48. The proximal portion 49 of the distal plunger portion 41 is engaged with the distal portion 47 of the proximal plunger portion 42 such that the distal plunger portion 41 can substantially freely rotate with respect to the proximal plunger portion 42 but has to make the same movements in distal or proximal direction as the proximal plunger portion 42.

The adjustment ring 48 is located between proximal and distal main body portions 11 and 12. Windows 14 are provided on opposite sides of main body 10 where the proximal and distal main body portions 11 and 12 meet.

The injection device 1 has a generally oval cross section. The windows 14 are provided on those "sides" of the oval which have the smaller distance from the centre of the oval. The main body is continuous on those "sides" of the oval which have the greatest distance from the centre of the oval. This means that the main body 10 with proximal and distal main body portions 11 and 12 can be formed (e.g. moulded) in one piece and further that adjustment ring 48 can project through windows 14 whilst being securely held within main body 10.

In order to adjust the dose to be injected the user can rotate adjustment ring 48, thereby rotating the plunger 40. As mentioned, this sets the axial position of stop member 44 along distal plunger portion 41. Through setting this axial position the user can determine how far the plunger is allowed to project into container portion 24. This is so because movement of the plunger in distal direction during the injection process is stopped when stop member 44 makes contact with the proximal end of container portion 24. The axial position of stop member 44 along distal plunger portion 41 (before the beginning of the injection operation) can be viewed by the user through a further window 16 provided in the distal main body portion 12. Suitable indications may be provided at window 16 to indicate to the user which dose corresponds to the set position of stop member 44 with respect to window 16.

EP-A-2633874 discloses a medicament delivery device comprising a housing, a safety sleeve movable between an extended position and a retracted position relative to the housing, a guide sleeve rotatably disposed in the housing, a plunger slidably disposed in the safety sleeve, and a button coupled to the housing. When the safety sleeve is in the retracted position, translation of the button relative to the housing causes the guide sleeve to rotate relative to the safety sleeve. Rotation of the guide sleeve relative to the safety sleeve allows the plunger to translate a predetermined axial distance relative to the safety sleeve.

SUMMARY OF THE INVENTION

In a first aspect the invention provides a substance delivery device for delivering a substance from a container, the device comprising a body, a plunger which is movable with respect to the body so as to expel at least a portion of a substance from a container, a trigger mechanism, a latch member latched in a stationary position at least along the longitudinal axis of the device before use, a lockout shroud being moveable along the longitudinal axis relative to the latch mechanism, wherein user manipulation of the trigger mechanism causes the latch mechanism to become unlatched and able to move along the longitudinal axis and to cause movement of a plunger relative to the body, and in a first position of the lockout shroud along the longitudinal axis relative to the latch member, the lockout shroud prevents the trigger mechanism from unlatching the latch member, whereas in a second position the lockout shroud allows the trigger mechanism to unlatch the latch member.

The lockout shroud may comprise one or more members configured, when the lockout shroud is in the first position, to prevent movement of one or more portions of the latch member, which in turn prevents the trigger mechanism from unlatching the latch member.

A needle guard may be accommodated at one end of the lockout shroud.

Before use of the device the end of the lockout shroud may stand proud of the needle guard and after the device is fired, the needle guard is retained by the lockout shroud but stands proud of the end of the lockout shroud.

The degree of movement between the plunger and the body may determine the amount of substance that is delivered and the device may comprises, an instance of one or more co-operating features associated with the plunger, and a corresponding instance of one or more co-operating features associated with the body, whereby co-operation between the two instances of co-operating features determines the degree of movement between the plunger and the body, wherein there is a plural instances of said one or more co-operating features associated with at least one of the plunger and the body, and co-operation between different instances of co-operating features allows different ranges of movement between the plunger and the body.

There may be a single instance of one or more co-operating features associated with one of the body and the plunger and plural instances of one or more co-operating features associated with the other of the plunger and the body.

The at least one instance of one or more co-operating features associated with the plunger may be located on an external surface of the plunger.

The at least one instance of one or more co-operating features associated with the body may be located on an internal surface of the body.

The plural instances of one or more co-operating features associated with one of the plunger and the body may each comprise one or more tracks, and the or each track of a first instance of the one or more co-operating features may be relatively long compared with the or each track of a further instance of the co-operating features.

A single instance of one or more co-operating features may comprise an instance of one or more pegs associated with one of the plunger and the body, the or each peg being configured to follow each said track.

Relative rotation of the plunger and body may determines which instance of one or more co-operating features associated with the body or the plunger is selected for co-operation with the corresponding instance of at least one co-operating feature associated with the other of the body and the plunger.

The device may further comprise a selector rotatable by a user for causing relative rotation of the plunger relative to the body.

The substance delivery device may comprise a container carrier housed within the body for receiving a substance container, wherein the container carrier is move-able along a longitudinal axis of the device relative to the body during a substance delivery process, wherein a surface of the container carrier includes at least one visual indicator that can be seen through a window in the body in at least one of the positions of the container carrier.

The container carrier may carry two visual indicators, at least one of the visual indicators is not visible to a user in at least one position of the container carrier.

The lockout shroud may be housed coaxially within the body of the device, the container carrier being housed within the lockout shroud and the lockout shroud comprises a cut out portion whereby a portion of the container carrier can be seen through the window of the body.

In a second aspect the invention provides a substance delivery device for delivering a substance from a container, the device comprising a body, a plunger which is movable with respect to the body so as to expel at least a portion of a substance from a container, a container carrier housed within the body for receiving a substance container, wherein the container carrier is move-able along a longitudinal axis of the device relative to the body during a substance delivery process, wherein and a surface of the container carrier includes at least one visual indicator that can be seen through a window in the body in at least one of the positions of the container carrier.

The container carrier may carry two visual indicators, at least one of the visual indicators is not visible to a user in at least one position of the container carrier.

The substance delivery device may further comprise a lockout shroud housed coaxially within the body of the device, the container carrier being housed within the lockout shroud and the lockout shroud comprises a cut out portion whereby a portion of the container carrier can be seen through the window of the body.

DETAILED DESCRIPTION OF THE INVENTION

Considering FIGS. 1 to 5, an injection device 1 is shown in accordance with the invention.

Figure 1:
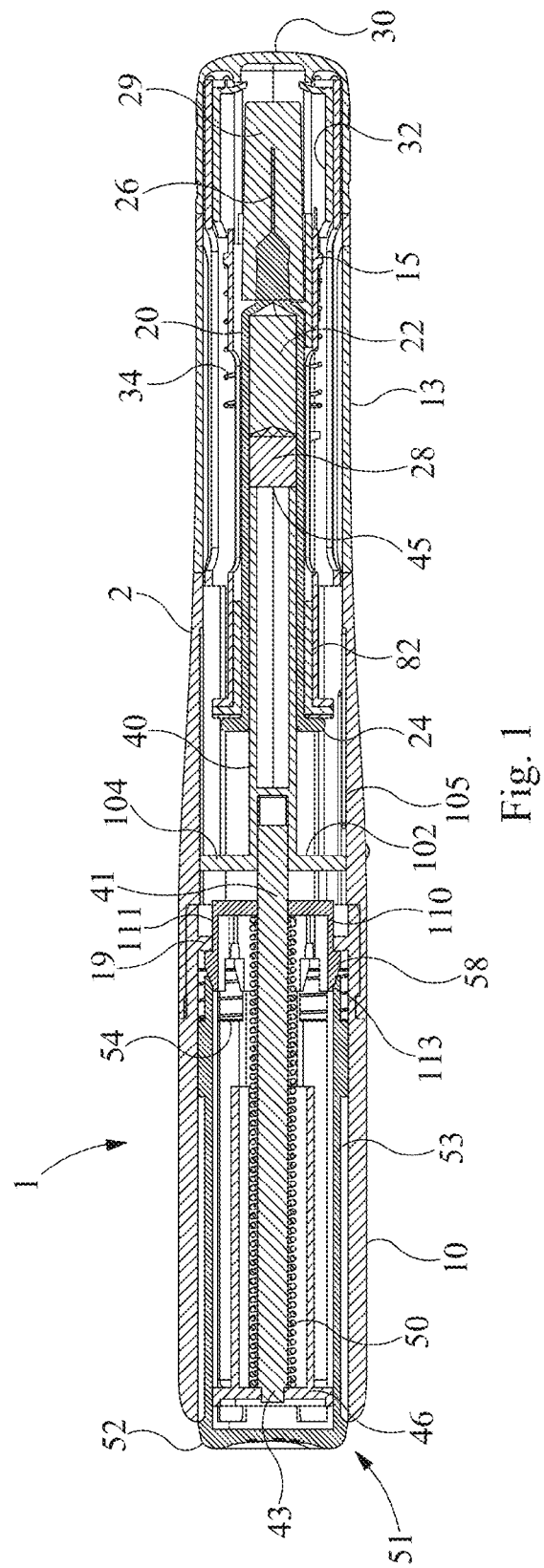
FIG. 1 is a cross section through an injection device according to the invention.
Figure 2:
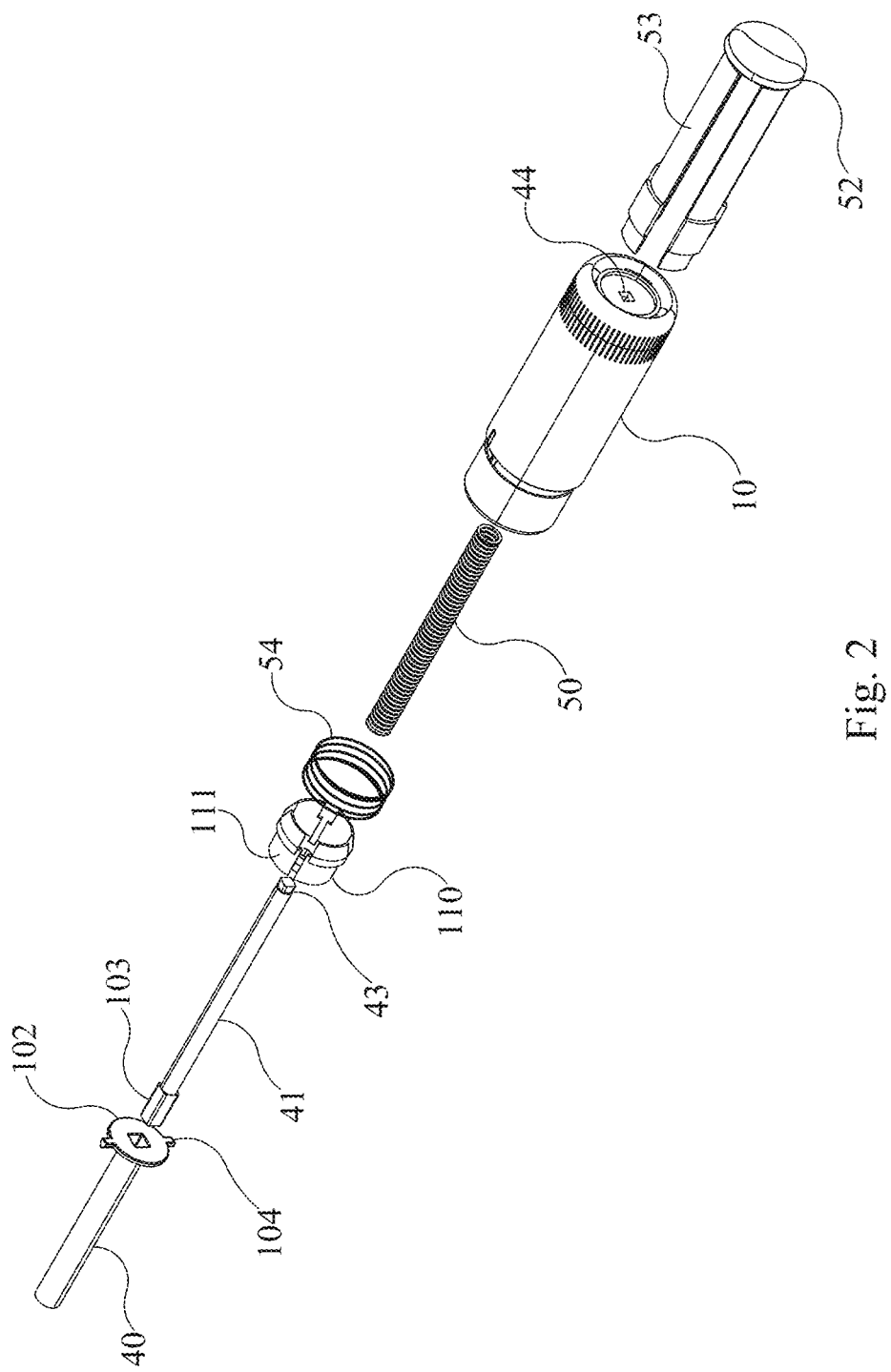
FIG. 2 is an exploded perspective view of a proximal portion of the device of FIG. 1.
Figure 3:
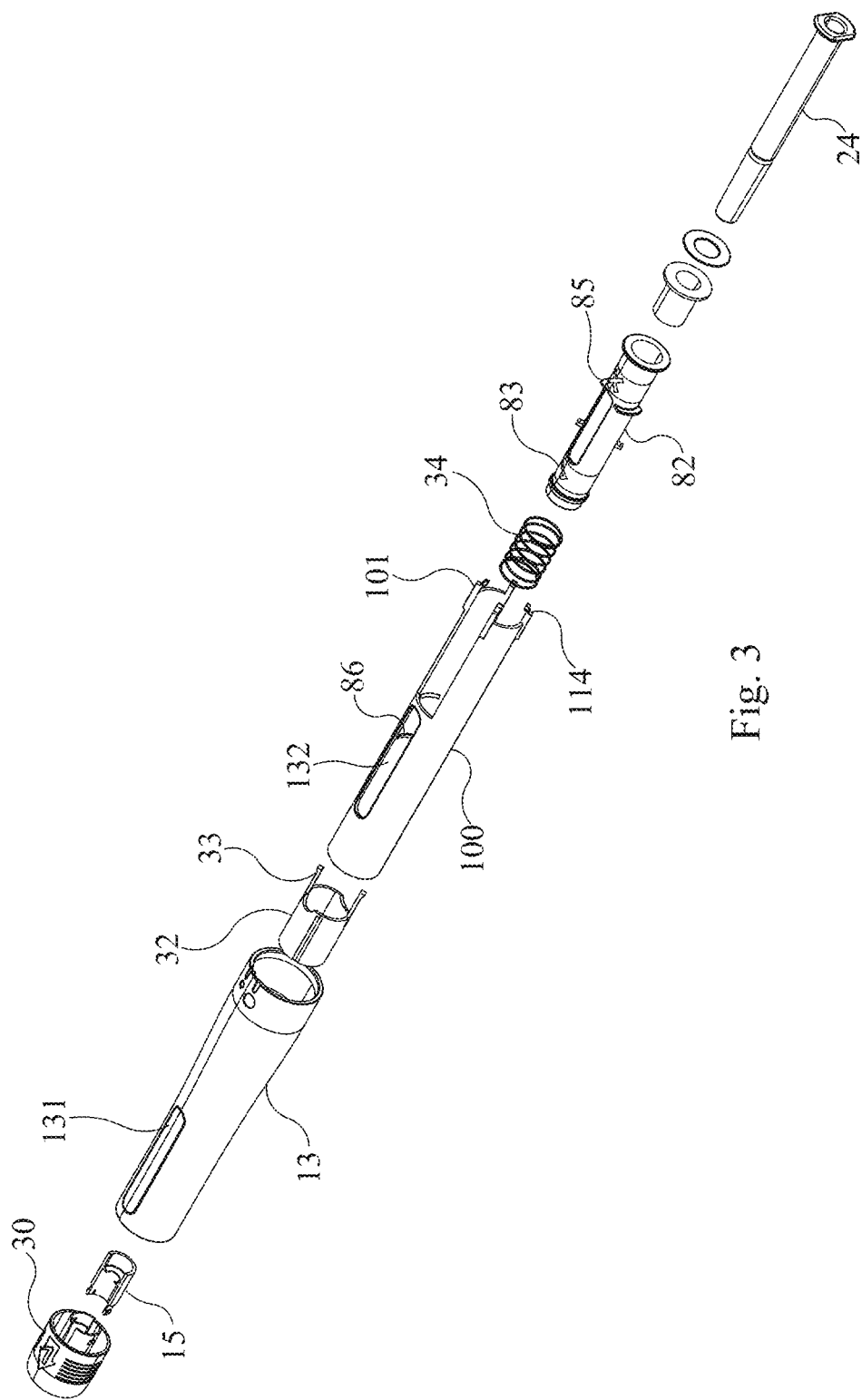
FIG. 3 is an exploded perspective view of a distal portion of the device of FIG. 1.
Figure 4A:
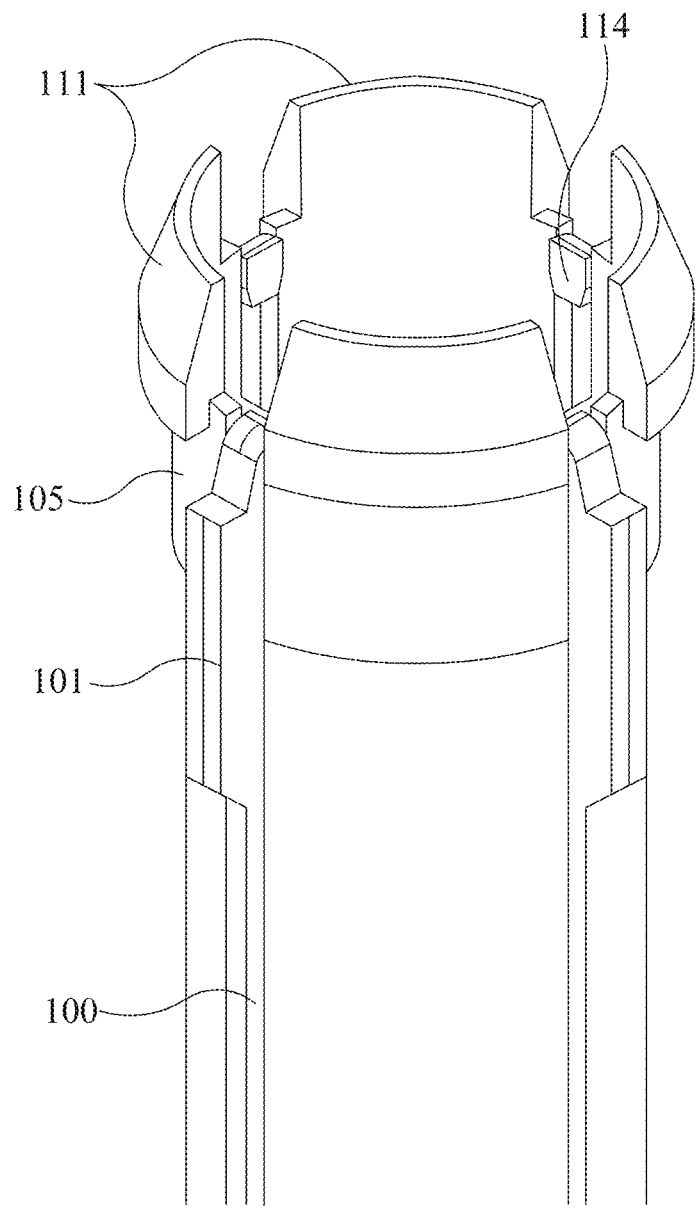
FIGS. 4a and 4b are detailed part views of the lockout shroud and latch ring.
Figure 4B:
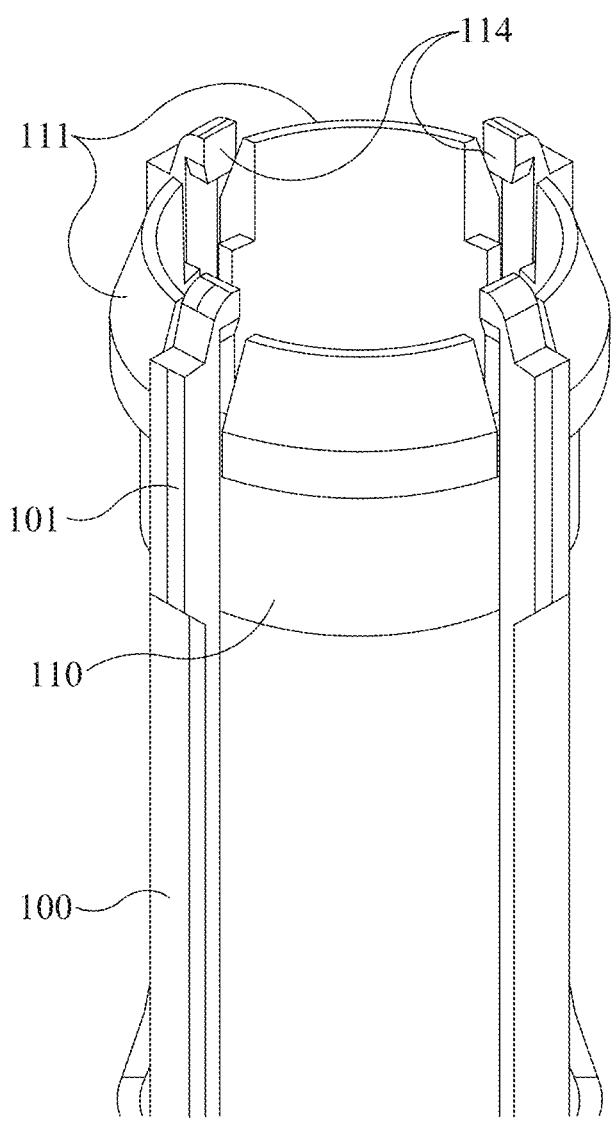
Figure 5:
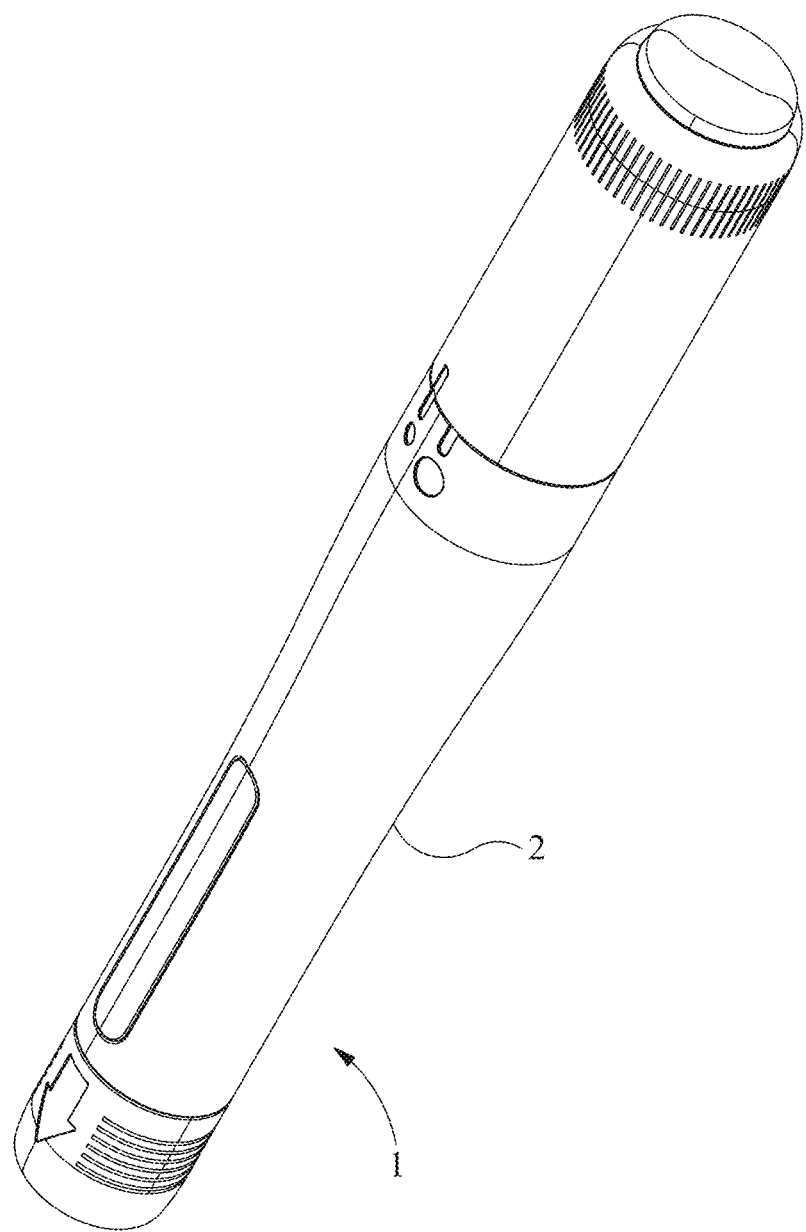
FIG. 5 is a perspective view of the device of FIG. 1.
Figure 6:
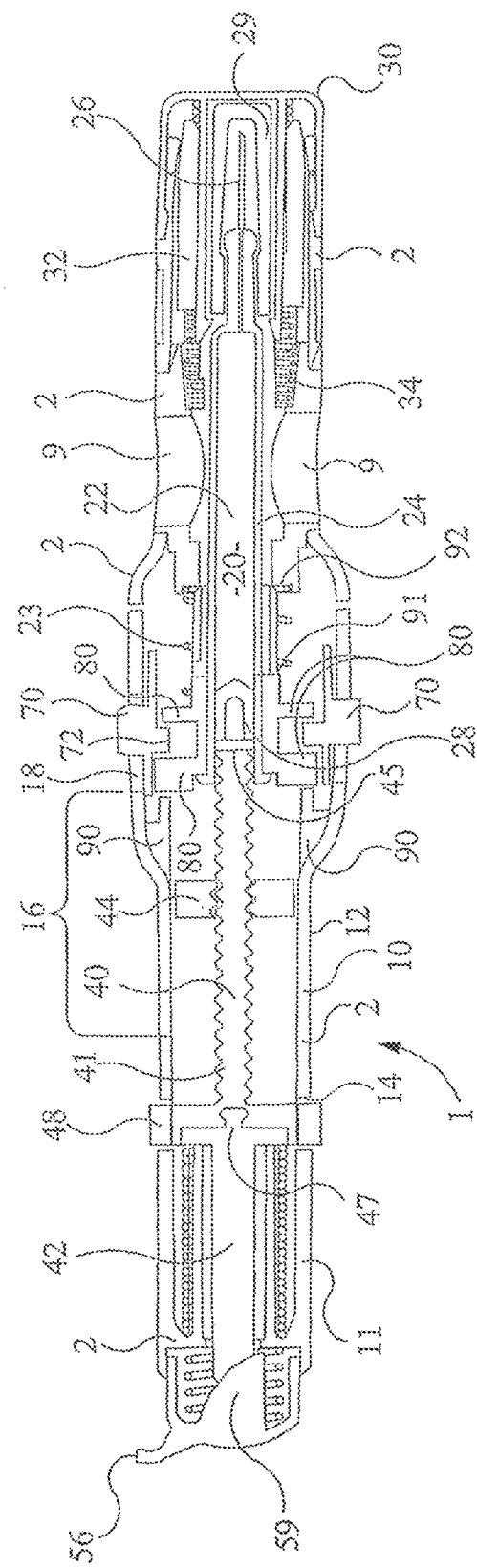
FIG. 6 is a cross section through a prior art injector pen.

FIG. 1 is a cross section through the whole device whereas FIGS. 2 and 3 are exploded perspective views of certain components of the device for ease of description. FIGS. 4a and 4b are enlarged view of a portion of a lockout shroud and a latch ring that co-operates with the lockout shroud as described below.

As can be seen from the exploded views the various part of the device fit together along a common longitudinal axis. The embodiment shown is a specific embodiment and is not intend to limit the manner in which the invention is implemented. For example, where some parts are shown as separate but would function mechanically if they were integral then the skilled person will recognise that both implementations are disclosed herein; similarly where certain parts are shown as integral but could be provided as two or more parts then such an implementation is also envisaged as falling within the present invention.

The main parts of the device 1 are the housing 2, including a main body 10, a mid-body 13, a shroud retainer 15, a needle guard 32, syringe carrier 82, syringe 20 including a container portion 24, plunger 40, a dose adjuster rod 41, firing spring 50 and trigger button 52. The dose adjuster rod in the present embodiment is fixed both rotationally and axially to the main body 10. The device also includes amongst other components, a lock out shroud 100 (shown in FIGS. 1 and 3) and an interlocking latch ring 110 (FIGS. 1 and 2).

Starting from the proximal end and considering FIGS. 1 and 2, a firing or trigger button 52 is received concentrically within the main body 10, together with the dose adjuster rod 41 and the firing spring 50. Dose adjuster rod 41 has its proximal end 43 connected to the main body 10; in this case the proximal end 43 is received by an opening 44 in a frame 46 formed at the proximal end of the main body 10. Rotation of the main body causes rotation of the dose adjuster rod 41 around its longitudinal axis.

The trigger button 52 co-operates with the latch ring 110. The latch ring 110 is held in place relative to the housing 2, before use, by shoulder 19 carried by the internal wall of the main body 10 of the housing 2, which co-operates with co-operating portions in the form of outwardly projecting teeth 58 on flexible fingers 111 of the latch ring 110. The trigger button 52 has flexible arms 53 with cam surfaces 113 that co-operate with cam surfaces on the flexible fingers 111 of the latch ring 110, such that movement of the trigger button 52 relative to the latch ring 110 in the distal direction (towards the needle end of the device) will flex the fingers 111 of the latch ring 110 inwardly releasing the co-operating portions 58 from the shoulder 19. During the process the trigger button moves relative to the main body 10 against the bias of a spring 54.

Once the latch ring 110 has been released during the above process, the trigger button 52 is prevented from further, significant, movement, distally relative to the housing 2 by the ends of the flexible arms of the trigger button 52 abutting the shoulder 19. Alternatively, further co-operating elements can be supplied on the trigger button 52 or housing 2, or both in order to prevent further movement of the trigger button on release of the latch ring 110. The latch ring 110 is then urged forcefully by the spring 50 in a distal direction axially of the housing 2. The latch ring 110 in turn acts on a proximal portion of the plunger 40.

In an initial condition the above process is prevented from occurring by the lockout shroud 100. A proximal end of the lock out shroud cooperates with the latch ring to prevent accidental firing of the device 1. In other words, there is a two stage firing process, which is described below.

Turning now to FIGS. 1 and 3; distal end of plunger 40 is received in container portion 24 of syringe 20. In turn, the container portion 24 is received within syringe carrier 82, and syringe carrier 82 is received within lockout shroud 100. The syringe 20, the syringe carrier 82, and lockout shroud 100 are all housed within the mid-body portion 13 of housing 2.

A safety cap or needle sheath remover 30 is provided at the distal end of injection device 1. In an embodiment the safety cap 30 is hooked over the proximal end of a needle sheath 29 protecting the needle before use so that, when safety cap 30 is removed, the needle sheath is removed as well. The safety cap 30 may be formed in 2 halves which are assembled around the needle sheath to avoid applying axial force to the needle sheath during assembly. In the present embodiment shown in FIGS. 1 and 3, a separate component 15 is provided that is formed as a clam shell or in this case half clam shell which is assembled around the needle sheath allowing the safety cap to be snap fit onto the component 15 without damaging the needle sheath.

A needle guard 32 is accommodated on the distal end of the lockout shroud 100 and is moveable therewith axially of the mid-body 13. A spring 34 is included to bias the needle guard 32 in a distal direction and the syringe carrier 82 in a proximal direction.

In the present embodiment the needle guard 32 has proximally extending legs 33 which engage with axially extending closed-ended grooves 35 within the lockout shroud 100. The legs 33 have outward protrusions which initially engage within deeper detents within the grooves which hold the guard in position relative to the lockout shroud. This allows the needle guard 32 to move a limited distance in a distal direction only once the detent engagement has been disengaged but to be constrained from becoming detached from the lockout shroud 100. As can be seen from FIG. 1, with the safety cap 30 in place, the lockout shroud stands proud of the needle guard 32 which is located within the lockout shroud.

Once the safety cap 30 is removed, pressure can be applied to the end of the lockout shroud 100 (in use by pressing the end of the device against the skin of the user), whereby the needle guard 32 and the lockout shroud 100 move axially relative to the housing 2 in the proximal direction.

As can be seen more clearly in FIGS. 4A and 4B, the flexible fingers 111 of the latch ring 110 are interspersed by slots which have a generally T-shaped profile, the head of the T-profile being at the proximal end of the latch ring 110. Before any movement of the lockout shroud 100 in the proximal direction (FIG. 4a), internally facing lugs 114 located at the ends of the legs 101 of the lockout shroud 100 engage with the flexible fingers 111 of the latch ring 110 in the region of the narrow part of the T-profile. This arrangement prevents inward flexing of the fingers 111 and movement of the trigger button 52 since it is necessary for the fingers 111 to flex inwards for the trigger button to move relative to the latch ring.

The application of sufficient pressure to the distal end of lockout shroud 100 causes movement of the needle guard 32 and the lockout shroud 100 relative to the housing 2. The latch ring 110 is prevented from movement in the proximal direction (relative to the housing 2) by its engagement with the trigger button 52 and the force of the loaded spring 52; thus the lockout shroud 100 also moves relative to the latch ring 110. The movement of the lockout shroud 100 against the bias of the spring 34 is sufficient to move the lugs 114 into the T-profile slots described by the fingers 111 of the latch ring 110 (FIG. 4b) allowing fingers 111 to flex inwards. The trigger button can now be pushed axially of the housing 2 in the distal direction causing the cam surfaces 113 to co-operate with the fingers 111 to cause inward flexing of the fingers 111 and disengaging teeth 58 from shoulder 19.

When both operations required to trigger the device to fire are performed, the spring 50 then urges the latch ring 110 to move distally relative to the housing 2, until it contacts the plunger 40 and then the plunger 40 is also urged forcefully in the distal direction relative to the housing 2. The syringe 20 and syringe carrier 82 also move relative to the housing 2, the lockout shroud 100 and consequently the needle guard 32. This movement proceeds a certain distance increasing the pressure on the spring 34 which acts between the syringe carrier 82 and the needle guard 32 until the needle guard 32 is knocked out of position relative to the lockout shroud 100 when sufficient pressure is built up in spring 34 (or the spring 34 is completely compressed becoming solid in which case the entire load from spring 50 then acts to knock the guard out of its detent previously keeping it in place relative to the lockout shroud 100). The geometry is chosen to make sure the forward movement of the syringe carrier 82 is subsequently halted before the needle guard 32 is driven into the user under a high force from spring 50. Forward movement of the syringe carrier 82 is halted when one or more engagement portions 85 on the syringe carrier 82 abut corresponding engagement portions 86 on the internal wall of the lockout shroud 100. The force of the drive spring 50 is then applied to the plunger 40, the syringe carrier 82, and the lockout shroud 100, whereas the needle guard 32 is biased lightly forward by spring 34 only. Subsequent axial movement of the plunger 40 is then relative to the container portion 24 and causes the substance in the container to be expelled through the cannula 26.

Removing the pressure on the distal end of the lockout shroud 100 allows the needle guard 32 to extend beyond the lockout shroud under bias of spring 34 so as to guard the cannula that now extends beyond the lockout shroud 100. In the present embodiment the syringe carrier 82 is prevented from returning to its original position by the force of the firing spring acting on the latch ring, the plunger, the syringe and the syringe carrier.

The above described arrangement with the interlocking latch ring 110 and lockout shroud 100 provide a novel arrangement for a device with a two stage firing process.

Alternatively, or in addition a latch button may be provided external of the housing to allow firing of the device without movement of the lockout shroud if present. Instead of moving a lockout shroud to allow movement of fingers 111, a latch button can effect movement of the shoulder or shoulders 19 (or a portion of the housing carrying the shoulder 19) so as to allow movement of the latch ring 110 relative to the housing.

The present embodiment will also be used to describe a novel variable dosing selection for an injection device that may be used in conjunction with the above arrangement or may be used in other arrangements where appropriate.

As most easily seen in FIG. 2, the plunger 40 includes a head 102 for receiving the dose adjuster rod 41. As can be seen the distal end 103 of the dose adjuster rod 41 is shaped so as to prevent rotation of the dose adjuster rod 41 relative to the plunger 40. The head 102 of the plunger 40 carries pegs 104, which are shaped to follow tracks 105 in the housing 2, principally in the mid-body 13.

During the firing process the pegs 104 follow the tracks 105 as the plunger 40 travels axially within the housing 2. The tracks 105 are of a length to provide a specific dose of substance to be expelled from the syringe 20. The plunger can only travel the length of the tracks 105 before coming to a stop as the pegs 104 abut the end of the tracks 105. By providing more than one set of tracks 105—each set of tracks providing a differing specific dose of substance to be delivered by the device—a simple means for selecting the dose to be delivered is provided.

Before triggering the device 1, the pegs 104 are located at the start of one set of tracks; that is they are aligned with a particular track pair, for example, long tracks providing a "full" dose of the substance contained in the syringe 20. Off set from the long track pair around the circumference of the internal surface of the mid-body 13 is another shorter track pair 105 (not shown). Rotating the main body and mid body relative to each other (for example, rotating the main body 10 relative to the mid-body 13 clockwise looking from proximal to distal) will align the line 120 with the small indicator circle rather than the big indicator circle in FIG. 4. This equates to selecting a small dose rather than a full dose. Internally, the rotation of the main body portion 10 relative to the mid-body portion 13 causes rotation of the dose adjuster rod 41 and hence rotation of the plunger 40 relative to the mid-body 13 and consequently the pegs 104 are no longer aligned with the long tracks 105 but now with the short tracks 105.

In this embodiment, the rotation of the two housing portions 10 and 13 relative to each other causes relative rotation of the plunger head 102 and plunger 40 to the mid-body 13, whereas the trigger button 52, and latch ring 110 rotate relative to the main body 10; that is the latch ring 110 is fixed relative to the mid-body 13 and does not rotate relative to the lockout shroud 100 and trigger button 52. Rotation of the main body 10, relative to the mid-body 13 causes rotation of the plunger 40 since the proximal end 43 of the dose adjuster rod 41 is connected to the frame 46 of the main body 10.

In an alternative embodiment, the dose selector could be provided as a separate part of the housing 2, whereby the rotation of the selector acted directly on the proximal portion of the plunger which then provided rotation of the distal portion of the plunger relative to the housing.

Of course, the head 102 with the pegs 104 could be provided at any suitable portion of the plunger or a separate component configured to operate on the plunger and move with the plunger relative to the housing 2—together with appropriate modifications in relation to the co-operating tracks in the housing 2. Whilst the co-operating tracks in the embodiment are provided in the wall of the mid-body portion of the housing, the tracks could be provided in any convenient manner, for example in a separate component located within the housing.

In the embodiment of FIGS. 1 to 4, the dose selector relies on pegs on the plunger located in one set of co-operating tracks, selected from 2 or more sets of such co-operating tracks. In an alternative embodiment the tracks are located on the plunger and pegs, ribs or other protrusions are located on the housing or otherwise arranged to co-operate with the tracks on the plunger so as to provide the required co-operation with the tracks. Any combination of tracks or protrusions is envisaged. The use of pegs on the plunger and tracks or grooves on the housing wall, provides a compact device.

When the device is triggered the latch ring 110 and plunger 40 all move axially in the distal direction. This movement also serves to move the syringe carrier 82 and syringe so as to protrude out of the needle guard 32 so that the skin of a user can be punctured by the cannula 26.

In a further aspect of the invention, the syringe carrier 82 carries indicator markings to indicate that the injector device is ready to be used or conversely that the device has already been used and should be discarded. Before use the ready-for-use indicator 83 (the tick mark on the distal portion of the syringe carrier shown in FIG. 3) is visible through a window 131 in the mid-body 13. In particular, the window 131 of the mid-body 13 is located relative to the syringe carrier 82 such that the ready-for-use indicator 83 can be seen through a distal portion of the window 131 before use of the device. A cut out 132 is required in the lockout shroud so that at least a portion of the syringe carrier 82 can be seen through the window 131.

Following the two-step procedure described above for firing the device, the syringe carrier 82 has moved relative to the lockout shroud 100 and the mid-body 13. The ready-for-use indicator 83 can no longer be viewed through the window 131 and/or through the cut-out 132 of the lockout shroud 100. On the other hand, a "used" indicator 84 can now be seen through a proximal portion of the window 131 and cutout 132.

Exemplary embodiments of the invention have been described with reference to the drawings. Modifications will suggest themselves to those skilled in the art without departing from the scope of the invention as defined by the appended claims.

The invention claimed is:

1. A substance delivery device for delivering a substance from a container, the device comprising:
  a body;
  a plunger which is movable with respect to the body so as to expel at least a portion of a substance from a container;
  a trigger mechanism;
  a latch member latched in a stationary position at least along the longitudinal axis of the device before use;
  a lockout shroud being moveable along the longitudinal axis relative to the latch mechanism,
  wherein user manipulation of the trigger mechanism causes the latch member to become unlatched and able to move along the longitudinal axis and to enable movement of a plunger relative to the body, and
  wherein i) in a first position of the lockout shroud along the longitudinal axis relative to the latch member, the lockout shroud prevents the trigger mechanism from unlatching the latch member, whereas ii) in a second position of the lockout shroud along the longitudinal axis relative to the latch member, the lockout shroud allows the trigger mechanism to unlatch the latch member,
  wherein a degree of movement between the plunger and the body determines an amount of substance that is delivered; and
  a first feature that co-operates with a second feature, the first feature being associated with the plunger, and the second feature being associated with the body,
  whereby co-operation between the first and second features determines the degree of movement between the plunger and the body, wherein there is a plurality of at least one of i) the first feature associated with the plunger, and ii) the second feature associated with the body,
and co-operation between different ones of the first feature and the second feature allows different ranges of movement between the plunger and the body,
wherein the plurality of the one of the first and second features each comprise one or more tracks, and the or each track of a first one of the one of the first and second features is relatively long compared with the or each track of a further one of the the one of the first and second features, and
wherein relative rotation of the plunger and body determines which one of the first and second features associated with the body and the plunger, is selected for co-operation with a corresponding one of first and second features associated with the other of the body and the plunger.

2. The substance delivery device as claimed in claim 1, wherein the lockout shroud comprises one or more members configured, when the lockout shroud is in the first position, to prevent movement of one or more portions of the latch member, which in turn prevents the trigger mechanism from unlatching the latch member.

3. The substance delivery device as claimed in claim 1, wherein a needle guard is accommodated at one end of the lockout shroud.

4. The substance delivery device as claimed in claim 3, wherein before use of the device the end of the lockout shroud stands from the needle guard and after the device is fired, the needle guard is retained by the lockout shroud but stands from the end of the lockout shroud.

5. The substance delivery device as claimed in claim 1, wherein there is a single one of the first feature associated with the plunger, and plural of the second feature associated with the body.

6. The substance delivery device as claimed in claim 1, wherein the first feature associated with the plunger is located on an external surface of the plunger.

7. The substance delivery device as claimed in claim 1, wherein the second feature associated with the body is located on an internal surface of the body.

8. The substance delivery device as claimed in claim 1, wherein there is a plurality of the first feature associated with the plunger, each first feature comprising the one or more tracks, and a single one of the second feature associated with the body, the second feature being a peg, the peg being configured to follow each of the one or more tracks of a selected one of the plurality of the first feature.

9. The substance delivery device as claimed in claim 1, wherein the device further comprises a selector rotatable by a user for causing relative rotation of the plunger relative to the body.

10. The substance delivery device as claimed in claim 1, further comprising a container carrier housed within the body for receiving a substance container, wherein the container carrier is moveable along a longitudinal axis of the device relative to the body during a substance delivery process, wherein a surface of the container carrier includes at least one visual indicator that can be seen through a window in the body in at least one of the positions of the container carrier.

11. The substance delivery device as claimed in claim 10, wherein the container carrier carries two visual indicators, at least one of the visual indicators is not visible to a user in at least one position of the container carrier.

12. The substance delivery device as claimed in claim 11, wherein the lockout shroud is housed coaxially within the body of the device, the container carrier being housed within the lockout shroud and the lockout shroud comprises a cut out portion whereby a portion of the container carrier can be seen through the window of the body.

13. The substance delivery device as claimed in claim 1, wherein there is plural of the first feature associated with the plunger, and a single one of the second feature associated with the body.

14. The substance delivery device as claimed in claim 1, wherein there is a plurality of the first feature associated with the body, each first feature comprising the one or more tracks, and a single one of the second feature associated with the plunger, the second feature being a peg, the peg being configured to follow each of the one or more tracks of a selected one of the plurality of the first feature.

15. A substance delivery device for delivering a substance from a container, the device comprising:
a body comprising plural sets of tracks of different length, each set of the tracks having a respective length to provide a different respective dose of substance to be expelled from the container;
a plunger which is movable with respect to the body so as to expel at least a portion of a substance from a container, the plunger carrying at least one peg that follows the tracks of the body so that during a firing process the at least one peg follows a selected set of the tracks as the plunger travels axially within the body;
a trigger mechanism;
a latch member latched in a stationary position at least along the longitudinal axis of the device before use;
a lockout shroud being moveable along the longitudinal axis relative to the latch mechanism,
wherein user manipulation of the trigger mechanism causes the latch member to become unlatched and able to move along the longitudinal axis and to enable movement of a plunger relative to the body along a selected set of the tracks, and
wherein i) in a first position of the lockout shroud along the longitudinal axis relative to the latch member, the lockout shroud prevents the trigger mechanism from unlatching the latch member, whereas ii) in a second position of the lockout shroud along the longitudinal axis relative to the latch member, the lockout shroud allows the trigger mechanism to unlatch the latch member,
wherein a degree of movement between the plunger and the body determines which set of the tracks the at least one peg travels and therefore the amount of substance that is delivered, and
wherein relative rotation of the plunger and body determines which set of tracks is selected for the at least one peg to travel during the firing process.

* * * * *